(12) United States Patent
Graves et al.

(10) Patent No.: US 7,355,504 B2
(45) Date of Patent: Apr. 8, 2008

(54) ELECTRICAL DEVICES

(75) Inventors: Gregory A. Graves, Troy, MI (US);
Michael Zhang, Taikoo Shing (CN);
Daniel Chandler, Menlo Park, CA
(US); Chi-Ming Chan, Kowloon (HK);
Shou-Mean Fang, Yokohama (JP);
Dennis Siden, Portola Valley, CA (US);
Mark Thompson, San Carlos, CA (US)

(73) Assignee: Tyco Electronics Corporation,
Middletown, PA (US)

( * ) Notice: Subject to any disclaimer, the term of this patent is extended or adjusted under 35 U.S.C. 154(b) by 0 days.

(21) Appl. No.: 10/721,478

(22) Filed: Nov. 25, 2003

(65) Prior Publication Data

US 2004/0246092 A1   Dec. 9, 2004

Related U.S. Application Data

(63) Continuation of application No. 09/181,028, filed on Oct. 27, 1998, now Pat. No. 6,651,315, which is a continuation of application No. 08/900,787, filed on Jul. 25, 1997, now Pat. No. 5,852,397, which is a continuation of application No. 08/727,869, filed on Oct. 8, 1996, now abandoned, which is a continuation of application No. 08/302,138, filed on Sep. 7, 1994, now abandoned, which is a continuation-in-part of application No. 08/152,070, filed on Nov. 12, 1993, now abandoned, and a continuation of application No. 08/121,717, filed on Sep. 15, 1993, now abandoned, which is a continuation of application No. 07/910,950, filed on Jul. 9, 1992, now abandoned.

(51) Int. Cl.
*H01C 7/10* (2006.01)

(52) U.S. Cl. .................... 338/22 R; 338/321

(58) Field of Classification Search ............. 338/22 R, 338/22 SD, 328, 331; 252/511–512; 219/521, 219/553
See application file for complete search history.

(56) References Cited

U.S. PATENT DOCUMENTS 2,482,316 A    9/1949   Bocking ................ 338/118

(Continued)

FOREIGN PATENT DOCUMENTS

DE    28 16 593    10/1979

(Continued)

OTHER PUBLICATIONS

Coombs, Printed Circuit Handbook, 1996, p. 24.1-24.17.

(Continued)

*Primary Examiner*—K. Richard Lee

(57) ABSTRACT

An electrical device which comprises first and second laminar electrodes and a laminar PTC resistive element sandwiched between them, the device comprising
  (a) a main portion which comprises a main part of the first electrode, a main part of the second electrode, and a main part of the resistive element; and
  (b) a first connection leg which extends away from the main portion and which comprises a first leg part of the first electrode which is integral with the main part of the first electrode, and a first leg part of the resistive element which is integral with the main part of the resistive element.

Such devices can be secured to circuit boards in a variety of ways, and to elastically deformed terminals. Preferably preferred devices contain two laminar electrodes, with a PTC element between them, and a cross-conductor which passes through the thickness of the device and contacts one only of the two electrodes. The cross-conductor permits connection to both electrodes from the same side of the device, and also makes it possible to carry out the steps for preparing such devices on an assembly which corresponds to a number of individual devices, with division of the assembly as the final step.

4 Claims, 9 Drawing Sheets

U.S. PATENT DOCUMENTS

| | | | |
|---|---|---|---|
| 3,221,145 A | 11/1965 | Hager, Jr. ................... 219/549 |
| 3,351,882 A | 11/1967 | Kohler et al. ............... 338/322 |
| 3,435,399 A | 3/1969 | Gielisse et al. ........... 338/22 R |
| 3,497,859 A | 2/1970 | Bang ......................... 338/309 |
| 3,648,364 A | 3/1972 | Endo ........................... 29/620 |
| 3,775,725 A | 11/1973 | Endo ......................... 338/262 |
| 3,835,434 A | 9/1974 | Kahn ....................... 338/22 R |
| 4,088,828 A | 5/1978 | Yamamoto et al. ......... 174/263 |
| 4,200,970 A | 5/1980 | Schonberger ................ 29/593 |
| 4,237,441 A | 12/1980 | van Konynenburg et al. ......................... 338/22 R |
| 4,238,812 A | 12/1980 | Middleman et al. ........ 361/106 |
| 4,255,698 A | 3/1981 | Simon ......................... 320/35 |
| 4,272,471 A | 6/1981 | Walker ....................... 264/104 |
| 4,304,987 A | 12/1981 | van Konynenburg ....... 219/553 |
| 4,315,237 A | 2/1982 | Middleman et al. ...... 338/22 R |
| 4,317,027 A | 2/1982 | Middleman et al. ........ 219/553 |
| 4,327,351 A | 4/1982 | Walker ..................... 338/22 R |
| 4,330,703 A | 5/1982 | Horsma et al. ............. 219/553 |
| 4,352,083 A | 9/1982 | Middleman et al. ......... 338/23 |
| 4,371,860 A | 2/1983 | May et al. ..................... 338/21 |
| 4,388,607 A | 6/1983 | Toy et al. ............... 338/22 SD |
| 4,426,633 A | 1/1984 | Taylor ........................ 338/25 |
| 4,434,416 A | 2/1984 | Schonberger ............... 338/203 |
| 4,445,026 A | 4/1984 | Walker ........................ 219/553 |
| 4,463,407 A | 7/1984 | Berger et al. ............. 361/306.1 |
| 4,475,138 A | 10/1984 | Middleman et al. .......... 361/58 |
| 4,486,737 A | 12/1984 | Ott ........................... 338/22 R |
| 4,486,738 A | 12/1984 | Sadlo et al. ................ 338/320 |
| 4,514,620 A | 4/1985 | Cheng et al. ................ 219/553 |
| 4,529,960 A | 7/1985 | Uchida et al. .............. 338/309 |
| 4,534,889 A | 8/1985 | van Konynenburg et al. ........................... 252/511 |
| 4,545,926 A * | 10/1985 | Fouts et al. .................. 252/511 |
| 4,560,498 A | 12/1985 | Horsma et al. ............. 252/511 |
| 4,591,700 A | 5/1986 | Sopory ....................... 219/505 |
| 4,593,181 A * | 6/1986 | Jensen et al. ............. 338/22 R |
| 4,605,471 A | 8/1986 | Mitchell ....................... 216/18 |
| 4,660,017 A | 4/1987 | Momoki et al. .............. 338/21 |
| 4,689,475 A | 8/1987 | Kleiner et al. ............. 219/553 |
| 4,706,060 A | 11/1987 | May .............................. 338/20 |
| 4,714,910 A | 12/1987 | Schwingenschuh et al. .. 338/21 |
| 4,724,417 A | 2/1988 | Au et al. .................. 338/22 R |
| 4,757,298 A | 7/1988 | Nishikawa et al. .......... 338/308 |
| 4,757,581 A | 7/1988 | Yamada et al. ............. 29/25.35 |
| 4,774,024 A | 9/1988 | Deep et al. .................. 252/511 |
| 4,777,718 A | 10/1988 | Henderson et al. ..... 338/312 X |
| 4,780,598 A | 10/1988 | Fahey et al. ................. 219/511 |
| 4,786,888 A | 11/1988 | Yoneda et al. ............ 338/22 R |
| 4,788,523 A | 11/1988 | Robbins ..................... 338/309 |
| 4,800,253 A | 1/1989 | Kleiner et al. .............. 219/553 |
| 4,801,784 A * | 1/1989 | Jensen et al. ............. 338/22 R |
| 4,811,164 A | 3/1989 | Ling et al. ................... 361/321 |
| 4,845,838 A | 7/1989 | Jacobs et al. ................ 29/671 |
| 4,861,966 A | 8/1989 | Matthiesen et al. ......... 219/205 |
| 4,873,508 A | 10/1989 | Ankenman et al. ........... 338/25 |
| 4,876,439 A | 10/1989 | Nagahori .................. 338/22 R |
| 4,882,466 A | 11/1989 | Friel ........................... 219/219 |
| 4,904,850 A | 2/1990 | Claypool et al. ............ 219/548 |
| 4,907,340 A | 3/1990 | Fang et al. ................ 29/610.1 |
| 4,924,074 A | 5/1990 | Fang et al. ................. 219/548 |
| 4,924,204 A | 5/1990 | Uchida ..................... 338/22 R |
| 4,924,205 A | 5/1990 | Caporali et al. ............. 338/227 |
| 4,935,156 A | 6/1990 | van Konynenburg et al. ........................... 219/553 |
| 4,937,551 A | 6/1990 | Plasko ...................... 338/22 R |
| 4,959,505 A * | 9/1990 | Ott ........................... 338/22 R |
| 4,977,309 A * | 12/1990 | Uchida ....................... 219/541 |
| 4,992,771 A | 2/1991 | Caporali et al. .......... 338/22 R |
| 4,993,142 A | 2/1991 | Burke et al. ................. 29/621 |
| 5,015,824 A * | 5/1991 | Monter et al. .............. 219/219 |
| 5,017,243 A | 5/1991 | Otsubo ...................... 136/244 |
| 5,049,850 A | 9/1991 | Evans et al. .............. 338/22 R |
| 5,057,811 A | 10/1991 | Strott et al. ............... 338/22 R |
| 5,085,364 A | 2/1992 | Ishikawa et al. ............ 228/139 |
| 5,089,801 A | 2/1992 | Chan et al. ............... 338/22 R |
| 5,142,263 A | 8/1992 | Childers et al. ............... 338/21 |
| 5,194,316 A | 3/1993 | Horner et al. .............. 428/195 |
| 5,196,136 A | 3/1993 | Dishart et al. .............. 252/170 |
| 5,210,516 A | 5/1993 | Shikama et al. .......... 338/22 R |
| 5,212,466 A | 5/1993 | Yamada et al. ........... 338/22 R |
| 5,216,404 A * | 6/1993 | Nagai et al. ............. 338/22 SD |
| 5,228,188 A | 7/1993 | Badihi et al. .................. 29/623 |
| 5,241,741 A | 9/1993 | Sugaya ........................ 29/612 |
| 5,247,277 A | 9/1993 | Fang et al. ................ 338/22 R |
| 5,258,738 A | 11/1993 | Schat ......................... 338/332 |
| 5,271,548 A | 12/1993 | Maiwald ..................... 228/175 |
| 5,280,263 A | 1/1994 | Sugaya ..................... 338/22 R |
| 5,291,535 A | 3/1994 | Baker et al. ................. 378/22 |
| 5,303,115 A | 4/1994 | Nayar et al. ................ 361/106 |
| 5,347,258 A | 9/1994 | Howard et al. ............. 338/333 |
| 5,351,390 A | 10/1994 | Yamada et al. ............... 29/612 |
| 5,451,921 A | 9/1995 | Crawford et al. ........... 338/220 |
| 5,831,510 A | 11/1998 | Zhang et al. ............. 338/22 R |
| 5,852,397 A * | 12/1998 | Chan et al. ............... 338/22 R |
| 6,606,023 B2 * | 8/2003 | Chiang et al. ............ 338/22 R |

FOREIGN PATENT DOCUMENTS

| | | |
|---|---|---|
| DE | 31 22 612 | 12/1982 |
| DE | 87 16 103 | 3/1988 |
| DE | 38 39 868 | 6/1989 |
| DE | 39 10 861 | 11/1989 |
| DE | 40 00 089 | 7/1990 |
| EP | 0 223 404 | 5/1987 |
| EP | 0 308 306 | 3/1989 |
| EP | 0 398 811 | 11/1990 |
| EP | 0461-864 A1 | 12/1991 |
| EP | 0 509 582 | 10/1992 |
| EP | 0 649 562 | 3/1998 |
| GB | 1415454 | 11/1975 |
| JP | 49-28594 | 8/1974 |
| JP | 55-126601 U | 3/1979 |
| JP | 54-73260 | 6/1979 |
| JP | 57-57502 U | 9/1980 |
| JP | 56-150802 | 11/1981 |
| JP | 61-124104 | 6/1986 |
| JP | 62-32505 U | 2/1987 |
| JP | 62-34404 U | 2/1987 |
| JP | 62-36502 U | 3/1987 |
| JP | 62-51706 U | 3/1987 |
| JP | 62-155501 A | 7/1987 |
| JP | 63-13302 A | 1/1988 |
| JP | 63-46802 U | 3/1988 |
| JP | 63-131116 U | 8/1988 |
| JP | 63-211701 | 9/1988 |
| JP | 63-216301 | 9/1988 |
| JP | 63-244702 | 10/1988 |
| JP | 01-95714 U | 6/1989 |
| JP | 1-259502 A | 10/1989 |
| JP | 2-131301 U | 10/1990 |
| JP | 2-146402 U | 12/1990 |
| JP | 3-123002 A | 5/1991 |
| JP | 3-201409 * | 9/1991 ............... 338/22 R |
| JP | 4-139704 A | 5/1992 |
| JP | 4-372101 A | 12/1992 |
| JP | 5-29111 | 2/1993 |
| WO | WO 84/01259 | 3/1984 |
| WO | WO 94/01876 | 1/1994 |
| WO | WO 95/08176 | 3/1995 |
| WO | WO 95/31816 | 11/1995 |

OTHER PUBLICATIONS

Harper, Electronic Packaging and Interconnection Handbook (1991), p. 1.37-1.43, 8.3-8.5, 8.53-8.56, 9.1-9.16, 9.41-9.49.
Standler, Protection of Electronic Circuits from Overvoltages, 1989, p.133.
U.S. Appl. No. 07/893626 (Chandler et al.), filed Jun. 5, 1992.
"Protection of Batteries with PolySwitch.RTM. Devices", Raychem Corporation, Jan., 1987.
Search Report for International Application No. PCT/US93/06480, dated Oct. 7, 1993.
Search Report for International Application No. PCT/US94/10137, dated Nov. 23, 1994.
Search Report for International Application No. PCT/US95/05567, dated Jun. 26, 1995.
Search Report for International Application No. PCT/US95/07420, dated Sep. 4, 1995.
"PolySwitch PTC Devices, Standard Product List", Raychem Corporation, May 1992.
"PolySwitch SMD Surface Mount devices PTC overcurrent protection" trade brochure, Raychem Corporation, Nov. 1992.
"PolySwitch SMD Installation Guidelines" trade brochure, Raychem Corporation, Nov. 1992.

* cited by examiner

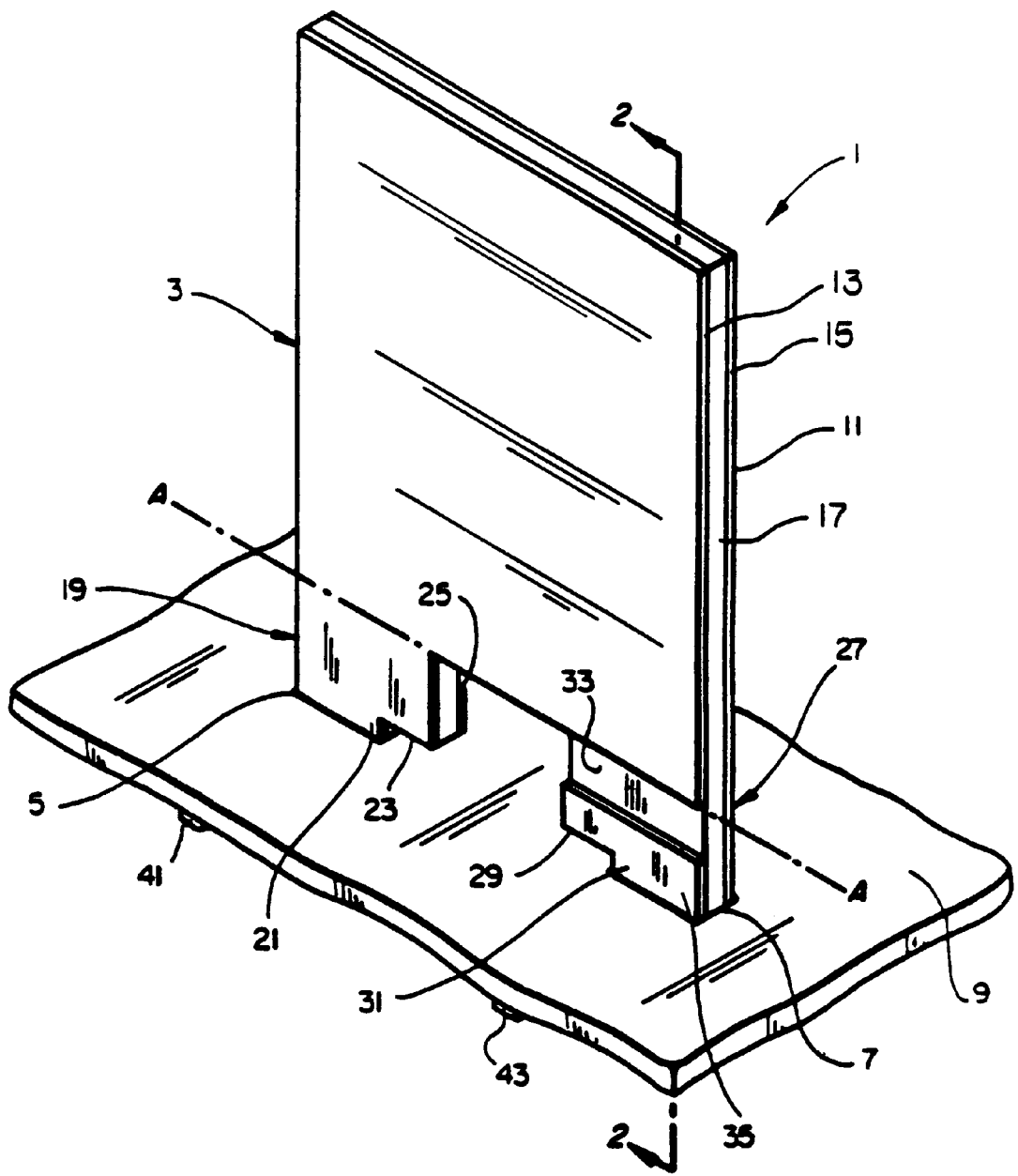
FIG_9

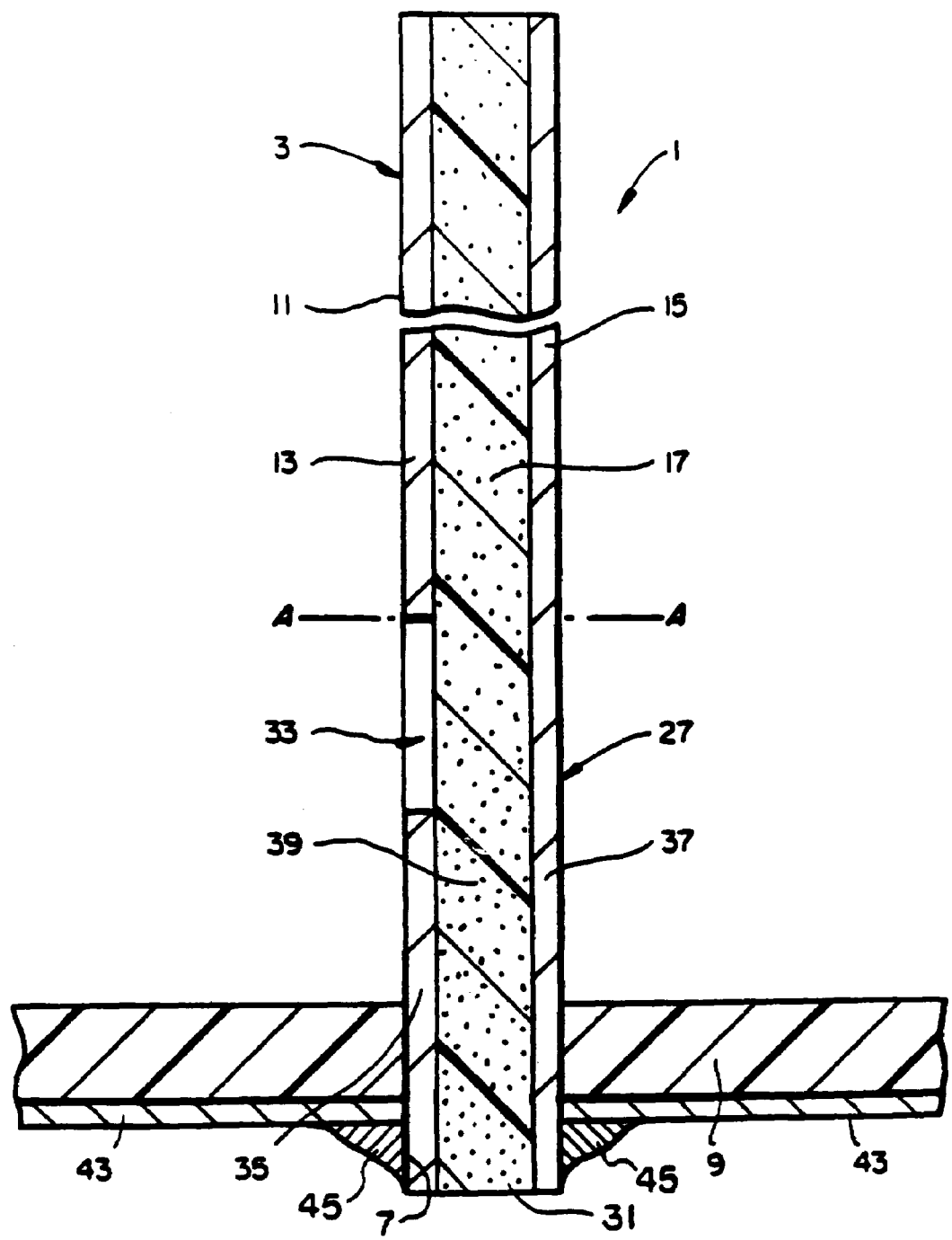
FIG_10

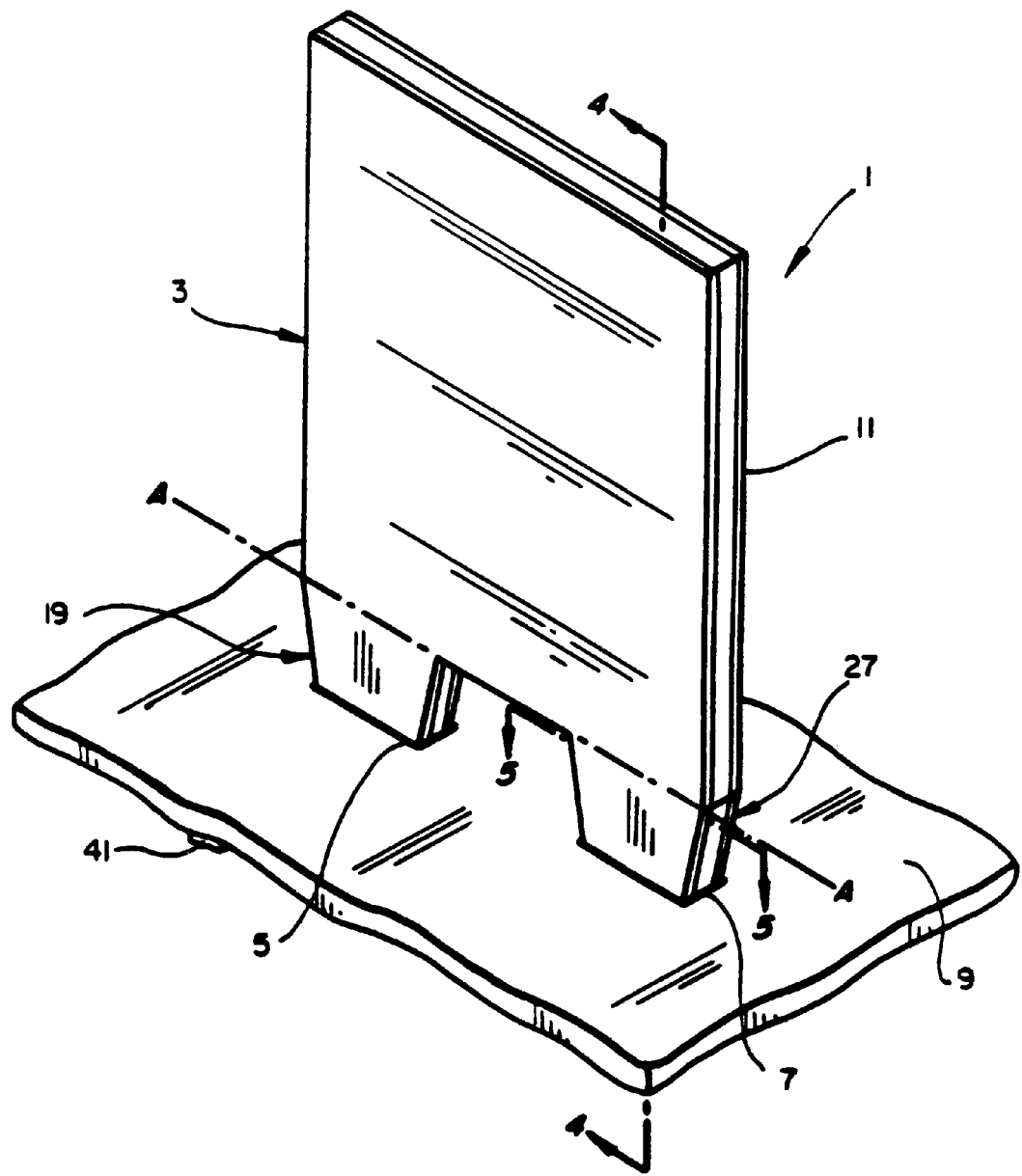
FIG_11

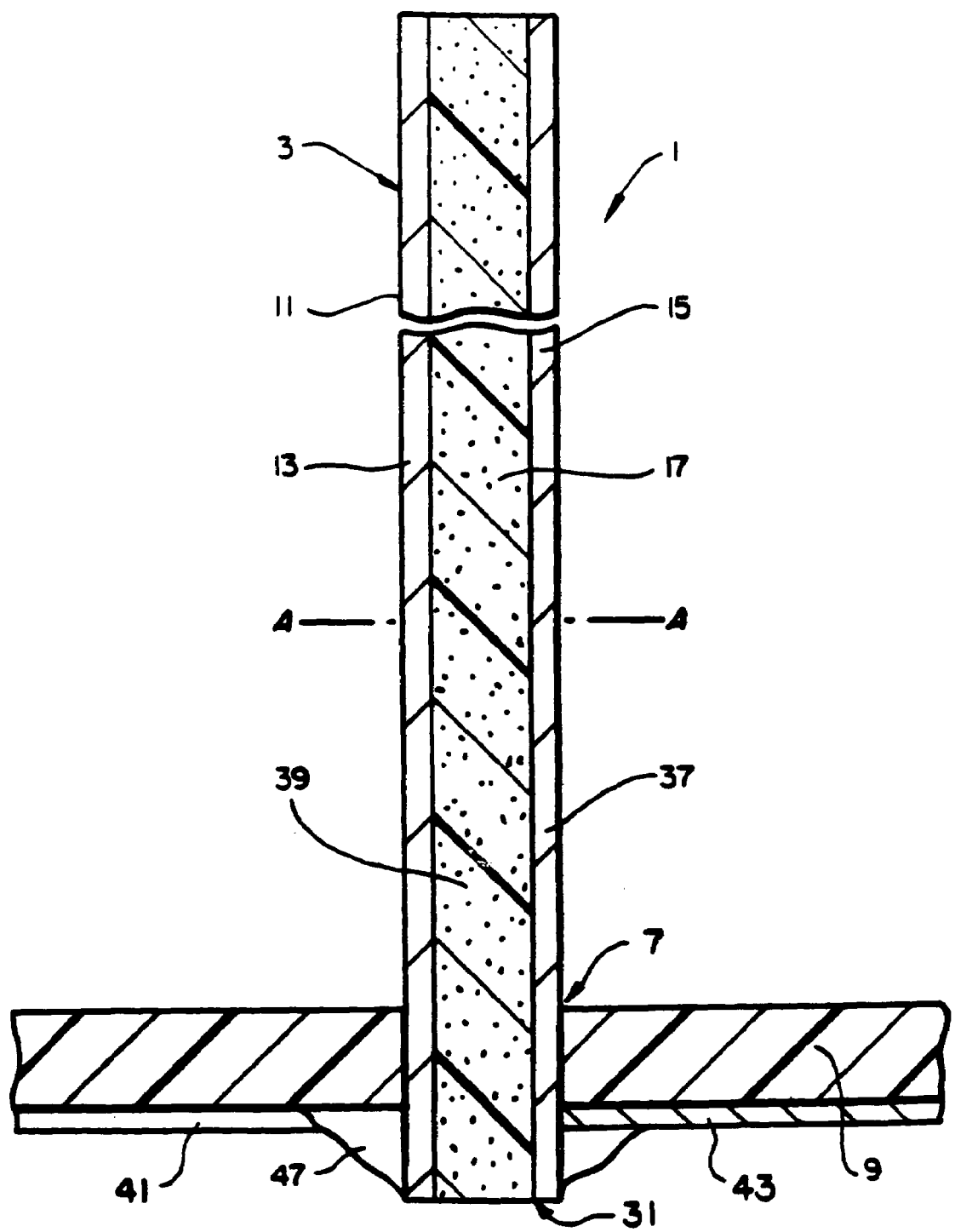
FIG_12

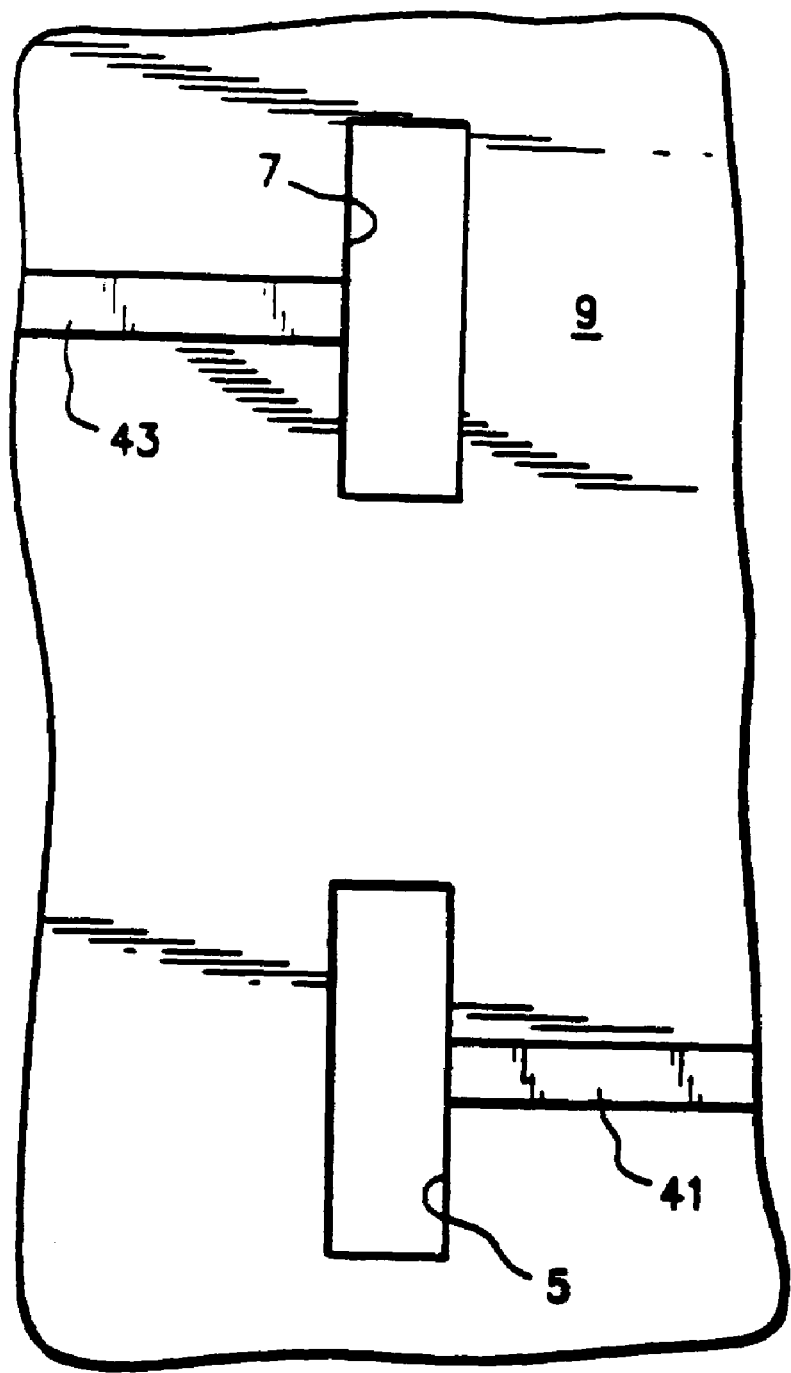
FIG_13

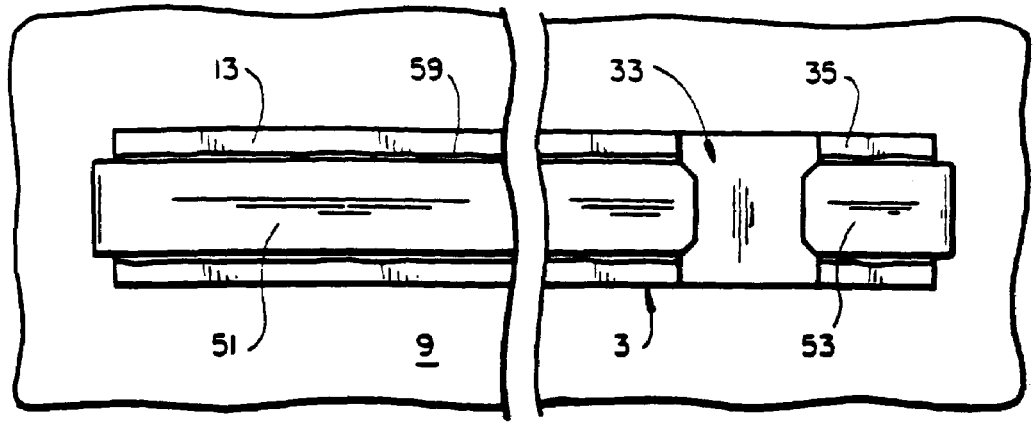
FIG_14
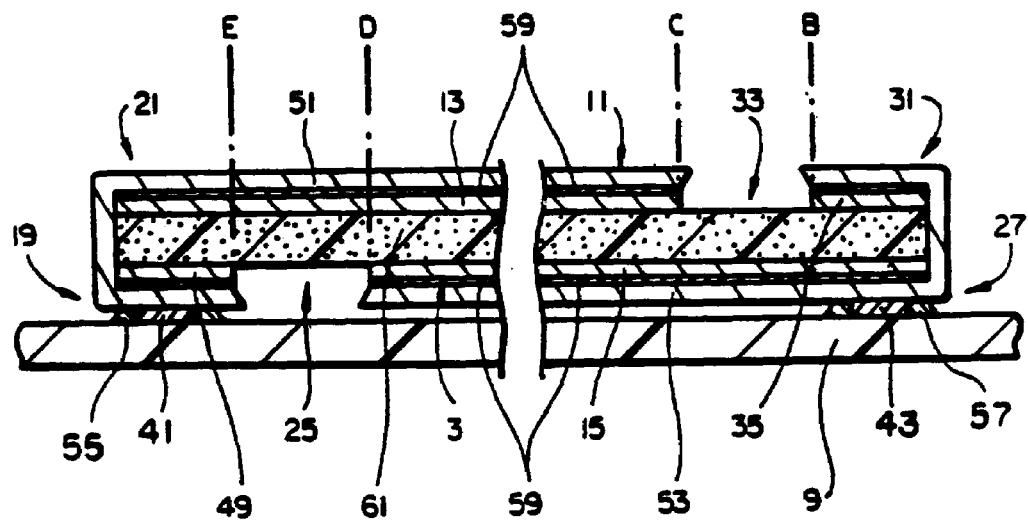
FIG_15

ELECTRICAL DEVICES

CROSS REFERENCE TO RELATED APPLICATIONS

This application is a continuation of U.S. patent application Ser. No. 09/181,028 filed Oct. 27, 1998, now U.S. Pat. No. 6,651,315, which is a continuation of U.S. patent application Ser. No. 08/900,787, filed Jul. 25, 1997, now U.S. Pat. No. 5,852,397, which is a continuation of U.S. patent application Ser. No. 08/727,869, filed Oct. 8, 1996, now abandoned, which is a continuation of U.S. patent application Ser. No. 08/302,138, filed Sep. 7, 1994, now abandoned, which is a continuation-in-part of (1), commonly assigned U.S. patent application Ser. No. 08/152,070, filed Nov. 12, 1993, by Graves, Zhang, Chandler, Chan and Fang, now abandoned, which is a file wrapper continuation of U.S. patent application Ser. No. 07/910,950, filed Jul. 9, 1992, now abandoned, and (2), commonly assigned U.S. patent application Ser. No. 08/121,717, filed Sep. 15, 1993, by Fang, Siden, Thompson and Zhang, now abandoned, the disclosures of which are incorporated herein by reference for all purposes.

This application is also related to copending International Application No. PCT/US93/06480, filed Jul. 8, 1993, by Raychem Corporation which claims priority from U.S. patent application Ser. No. 07/910,950, to commonly assigned U.S. patent application Ser. No. 08/242,916, filed May 16, 1994, by Zhang and Fang, now abandoned if favor of U.S. application Ser. No. 08/710,925, now U.S. Pat. No. 5,831,510, and to commonly assigned U.S. patent application Ser. No. 08/257,586, filed Jun. 9, 1994, by Zhang, Thompson, Toth and Beadling, now abandoned in favor of U.S. application Ser. No. 08/808,135, now U.S. Pat. No. 5,864,281. The entire disclosure of each of those U.S. and International patent applications is incorporated herein by reference for all purposes.

BACKGROUND OF THE INVENTION

1. Field of the Invention
This invention relates to electrical devices.
2. Introduction to the Invention
Many electrical devices comprise two laminar electrodes and, sandwiched between them, an electrical element which may be a conductor, e.g. a resistive element, as for example in a resistor or a varistor, or a non-conductor, as for example in a capacitor. Particularly useful devices of this type are circuit protection devices which comprise a laminate of two laminar electrodes and, sandwiched between the electrodes, a laminar resistive element which exhibits PTC behavior. The resistive element may be composed of conductive polymer (this term being used to denote a composition comprising a polymer and, dispersed, or otherwise distributed, therein, a particulate conductive filler) or a ceramic, e.g. a doped barium titanate. When a conductive polymer is used, such devices are generally prepared by stamping (or otherwise cutting) a plurality of the devices out of a laminate of a sheet of the conductive polymer between two metal foils. When a ceramic is used, such devices are usually prepared by applying liquid electrode material to the major surfaces of a preformed laminar resistive element, and solidifying the liquid electrode material.

The products of such processes can sometimes be used without the addition of electrical leads, for example by installation between two spring-loaded terminals. In most cases, however, an electrical lead must be secured to each of the laminar electrodes, so that the device can be connected to other components of a circuit, e.g. mounted on a circuit board. The addition of leads is an additional expense and usually involves heating (e.g. during soldering or welding) which can cause damage, particularly to conductive polymer elements. The latter problem is particularly severe when a conductive polymer is heated a second time when the leads are connected to other circuit elements, in particular when the leads are connected to a printed circuit board by a soldering process. A further problem which can arise when such devices are to be mounted on a printed circuit board is that they protrude further from the board than is desirable.

SUMMARY OF THE INVENTION

We have now realized, in accordance with the present invention, that when at least one of the laminar electrodes of an electrical device as described above is to be connected to an electrical conductor on an insulating substrate, in particular a printed circuit board, then by appropriate modification of the device and/or of the configuration of the electrical conductor on the substrate, the connection can be made either without the need for a lead (or other connecting member), or with the aid of a connecting member which is electrically connected to the electrode in the same step as it is electrically connected to the conductor on the substrate. We have also realized, in accordance with the present invention, that such modification can also be extremely valuable for electrical devices which are connected via elastically deformed terminals. The invention will be described herein chiefly by reference by circuit protection devices comprising a laminar PTC resistive element sandwiched between, and preferably contacted directly by, two laminar electrodes, but it is also applicable to other devices comprising two laminar electrodes and another type of laminar element sandwiched between them.

Typically, the devices of the invention have, in addition to a main portion having a normal configuration (typically a simple geometric shape such as a rectangle or a circle), at least one connection leg which extends away from the main portion and which comprises an extension of the PTC resistive element and an extension of one of the electrodes secured to the PTC element. The connection leg can, but preferably does not, also contain an extension of the other electrode.

In one use of such modified devices, the device is mounted on a circuit board by inserting the end of the connection leg into an aperture in the board and soldering the electrode to a metal conductor which is secured to the board and which leads to the aperture. If the connection leg does not include extensions of both electrodes, then the solder connection can be carried out in conventional ways. If the leg does include extensions of both electrodes in the region of the aperture, then care must be taken to ensure that the solder connects only the desired electrode to the metal conductor. For this purpose, the metal conductor can lead to one side only of the aperture and preferably can be substantially narrower than the aperture and the face of the connection leg to which it is soldered. A circuit board having a metal conductor and an aperture of this kind is believed to be novel per se and as such forms a part of the present invention. Generally, a device which is to be mounted in this way will be modified so that it has two connection legs of the kind described, extending in the same direction from the main portion of the device, so that the legs can be mounted in adjacent apertures in the same circuit board. The legs preferably have distal portions which are inserted into the apertures in the board, and intermediate stand-off portions which cannot pass through the apertures and which ensure that the main part of the device is spaced apart from the board.

As discussed above (and in greater detail below), when the device is to be mounted in apertures in a circuit board, the connection leg can comprise extensions of both electrodes; preferably, however, the connection leg includes a bridge portion which extends across the full width of the leg and which includes only one of the electrodes, so that the device can be soldered to a conventional circuit board in the conventional way. When the connection leg is of the latter kind, the device can be mounted in the apertures of a circuit board as outlined above, or can be mounted flat on top of a circuit board.

To mount the device flat on top of a circuit board, the device is placed on the substrate with the electrode which extends into the connection leg on top. The bottom electrode is connected directly to a conductor on the board. The top electrode is connected to another conductor on the board by means of a connection member secured to the top electrode and extending downwards below the lower face of the PTC (or other) element. In a particularly preferred embodiment, the connection member is a transverse conductive member which passes through the PTC (or other) element; such a transverse member is often referred to herein as a "cross-conductor". The connection member is preferably electrically connected to the upper electrode before it is electrically connected to the conductor on the board; alternatively, both electrical connections can be made simultaneously. If there are two connection legs, one containing an extension of one of the electrodes only, and the other containing an extension of the other of the electrodes only, the device can be placed on the board with either electrode on top, and if the device is symmetrical, the connections to the device and the subsequent operation of the device can be the same.

The novel devices of the invention can be made by securing electrodes of appropriate shapes to resistive elements of the desired final shape; or by securing electrode precursors of appropriate shapes to resistive elements which are larger than the desired final shape, and then dividing the assembly into a plurality of devices of the desired final shape or shapes; or by preparing a plurality of devices of the desired final shape or shapes by division of a simple laminate of constant cross-section and, if desired or necessary, and before or after the division, removing unwanted portions of one or both of the electrodes. Such removal can be effected for example by milling or by etching. Preferably such removal of unwanted portions of the electrodes removes little or none of the PTC resistive element, which provides desirable physical strength to the connection leg. Preferably also, when, as is preferred, the connection leg includes an extension of only one of the electrodes, the leg does also include a residual portion of the second electrode. The residual portion is not electrically connected to the main portion, but provides valuable physical properties, including strength and resistance to deformation when connection to the first electrode is made by a spring clip or other elastically deformed terminal. A preferred process for preparing devices of the invention is described in copending, commonly assigned U.S. patent application Ser. No. 08/257,586, abandoned in favor of U.S. application Ser. No. 08/808,135, now U.S. Pat. No. 5,864,281, incorporated by reference herein.

The devices of the invention which contain at least one cross conductor which passes though the resistive element can be made by processes in which the various operative steps are carried out on an assembly which corresponds to a plurality of devices in both the longitudinal and the lateral dimension, and which, as the final step of the process, is divided into a plurality of devices. The ability to prepare devices in this way becomes increasingly important as the size (and, therefore, resistance) of the device decreases and this invention is especially valuable for preparing devices which are to be mounted on circuit boards and in other situations in which the smaller the size and resistance of the device, the better. For example, such a process can be used to make circuit protection devices having a surface area of about 0.02 inch$^2$ (13 mm$^2$) or even less.

The various steps of the process are preferably carried out at a temperature substantially below the melting point of the PTC element, in order to minimize changes in its electrical properties.

In one preferred aspect, this invention provides a novel assembly which comprises
  (1) a PTC resistive element which
    (a) is composed of a resistive material which exhibits PTC behavior,
    (b) has a first face and a second face, and
    (c) defines an aperture which runs between the first and second faces;
  (2) a transverse conductive member which
    (a) lies within the aperture defined by the PTC element,
    (b) runs between the first and second faces of the PTC element, and
    (c) is secured to the PTC element; and
  (3) a first laminar conductive member which (a) is secured to the first face of the PTC element and (b) is physically and electrically connected to the transverse conductive member.

This novel assembly can be
  (i) an electrical device which is ready for connection (the first laminar conductive member then providing the first electrode, and the device including also a second electrode which is not electrically connected to the cross-conductor), or
  (ii) a structure which (if necessary after further processing) can be divided into a plurality of electrical devices, each of the devices containing at least one cross-conductor.

In another preferred aspect, this invention provides an electrical assembly which comprises
  (A) a printed circuit board including first and second conductive traces on a surface thereof, and
  (B) an electrical device which comprises
    (1) a laminar PTC resistive element which
      (a) is composed of a resistive material which exhibits PTC behavior, and
      (b) has a first face and a second face;
    (2) a first laminar electrode which is secured to the first face of the PTC element;
    (3) a second laminar electrode which is secured to the second face of the PTC element;
    (4) an additional laminar conductive member which (a) is secured to the second face of the PTC element and (b) is spaced apart from the second electrode;
    the PTC element, the first electrode and the additional laminar conductive member defining an aperture which runs between the first electrode and the additional conductive member, through the PTC element; and (5) a transverse conductive member which
  (a) lies within the aperture, and
  (b) is physically and electrically connected to the first electrode and the additional conductive member;

said electrical device being placed on the printed circuit board and parallel thereto, with the first conductive trace physically and electrically connected to the additional conductive member, and the second conductive trace physically and electrically connected to the second electrode.

In another preferred aspect, this invention provides a method of making electrical devices which comprises
(A) providing an assembly which corresponds to a plurality of the electrical devices and which comprises
  (1) a laminar PTC resistive element which (i) is composed of a resistive material exhibiting PTC behavior, and (ii) has a first face and a second face,
  (2) a first laminar conductive member which is secured to the first face of the PTC element, and
  (3) a second laminar conductive member which is secured to the second face of the PTC element;
(B) making a plurality of apertures through the thickness of the assembly provided in step (A), the apertures being arranged in a regular pattern;
(C) simultaneously with step (B), or after step (B), placing a plurality of transverse conductive members within the apertures, in electrical contact with the first laminar conductive member;
(D) removing predetermined portions of at least one of the first and second conductive members; and
(E) after steps (A) to (D), dividing the assembly into a plurality of electrical devices, each device comprising
  (1) a part of the PTC resistive element,
  (2) a part of the first laminar conductive member, said part providing a first electrode,
  (3) a part of the second laminar conductive member, said part providing a second electrode,
  (4) a residual part of the second laminar conductive member, and
  (5) at least one transverse conductive member which electrically connects the residual part and the first electrode.

In this method, step (D) can be carried out before or after step (B) or before or after step (C).

When the PTC material is a conductive polymer, this method preferably makes use of a novel assembly which forms part of the present invention, namely an assembly which comprises
  (1) a laminar PTC resistive element which (i) is composed of a conductive polymer exhibiting PTC behavior, and (ii) has a first face and a second face,
  (2) a first laminar conductive member which is secured to the first face of the PTC element, and
  (3) a second laminar conductive member which is secured to the second face of the PTC element;

the PTC element and the first and second laminar conductive members defining a plurality of apertures which pass through the thickness of the assembly, and the apertures being arranged in a regular pattern.

In this assembly, preferably
  (a) the apertures are arranged in a plurality of straight lines, and
  (b) the first laminar conductive member is in the form of a plurality of strips which are parallel to each other and to the lines of apertures.

It is particularly preferred that
  (a) each strip of the first conductive member contains two adjacent lines of apertures, and
  (b) the second laminar conductive member is also in the form of a plurality of strips which are parallel to each other and to the lines of apertures, with each strip containing two adjacent lines of apertures, one of said lines of apertures falling within a first strip of the first conductive member and the other line of apertures falling within a second strip of the first conductive member.

BRIEF DESCRIPTION OF THE DRAWING

The invention is illustrated in the accompanying drawings, in which

FIG. 9 shows a plan view of another electrical assembly of the invention showing an electrical device of the invention mounted in the apertures of a circuit board and at right angles to the board;

FIG. 10 is a cross-sectional view of an assembly of the invention along line 2—2 of FIG. 9;

FIG. 11 is a plan view of another electrical assembly of the invention showing an electrical device of the invention mounted in the apertures of a circuit board and at right angles to the board;

FIG. 12 is a cross-sectional view of an assembly of the invention along line 4—4 of FIG. 11;

FIG. 13 is a bottom view of the assembly of FIG. 11;

FIG. 14 is a top view of another assembly of the invention which includes an electrical device of the invention mounted on a circuit board and parallel thereto; and FIG. 15 is a cross-sectional view through the thickness of the assembly of FIG. 14.

DETAILED DESCRIPTION OF THE INVENTION

Figure 1:
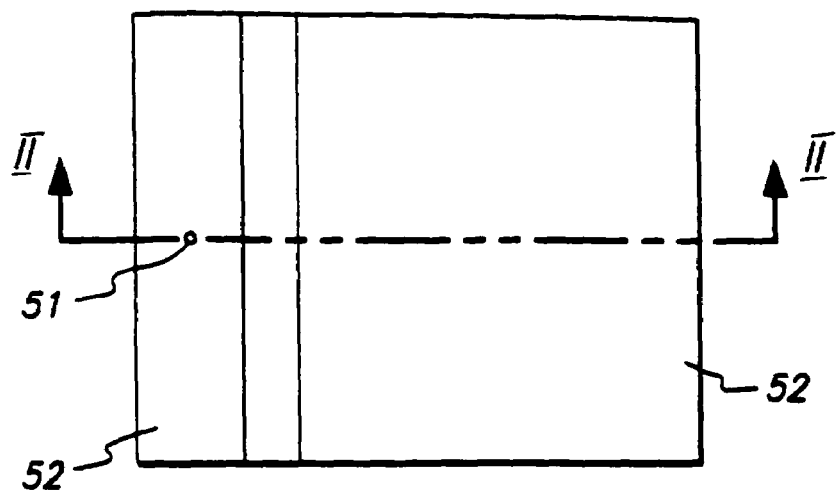
FIGS. 1 and 2 are plan and cross sectional views of a device of the invention containing a cross-conductor.

All embodiments and aspects of the invention set out below are to be regarded as part of Applicants' invention, even where the following detailed description is broader than the summary of the invention set out above. Conversely, the following detailed description should not be regarded as in any way limiting the generality of the summary of the invention set out above.

As described and claimed below, and as illustrated in the accompanying drawings, the present invention can make use of a number of particular features. Where such feature is disclosed in a particular context or as part of a particular combination, it can also be used in other contexts and in other combinations, including for example other combinations of two or more such features.

PTC Compositions

The PTC compositions used in the present invention are preferably conductive polymers which comprise a crystalline polymer component and, dispersed in the polymer component, a particulate filler component which comprises a conductive filler, e.g. carbon black or a metal. The filler component may also contain a non-conductive filler, which changes not only the electrical properties of the conductive polymer but also its physical properties. The composition can also contain one or more other components, e.g. an antioxidant, crosslinking agent, coupling agent or elastomer. For use in circuit protection devices, the PTC composition preferably has a resistivity at 23° C. of less than 50 ohm-cm, particularly less than 10 ohm-cm, especially less than 5 ohm-cm. Suitable conductive polymers for use in this invention are disclosed for example in U.S. Pat. No. 4,237,441 (van Konynenburg et al), U.S. Pat. No. 4,304,987 (van Konynenburg), U.S. Pat. No. 4,388,607 (Toy et al), U.S. Pat. No. 4,514,620 (Cheng et al), U.S. Pat. No. 4,534,889 (van Konynenburg et al), U.S. Pat. No. 4,545,926 (Fouts et al), U.S. Pat. No. 4,560,498 (Horsma et al), U.S. Pat. No. 4,591,700 (Sopory), U.S. Pat. No. 4,724,417 (Au et al), U.S. Pat. No. 4,774,024 (Deep et al), U.S. Pat. No. 4,935,156 (van Konynenburg), and U.S. Pat. No. 5,049,850 (Evans et al), and copending, commonly assigned U.S. patent application Ser. No. 07/893,626 (Chandler et al, filed Jun. 5, 1992), now abandoned. The disclosure of each of these patents and applications is incorporated herein by reference.

The PTC resistive element is preferably a laminar element, and can be composed of one or more conductive polymer members, at least one of which is composed of a PTC material. When there is more than one conductive polymer member, the current preferably flows sequentially through the different compositions, as for example when each composition is in the form of a layer which extends across the whole device. When there is a single PTC composition, and the desired thickness of the PTC element is greater than that which can conveniently be prepared in a single step, a PTC element of the desired thickness can conveniently be prepared by joining together, eg. laminating by means of heat and pressure, two or more layers, eg. melt-extruded layers, of the PTC composition. When there is more than one PTC composition, the PTC element will usually be prepared by joining together, eg. laminating by means of heat and pressure, elements of the different compositions. For example, a PTC element can comprise two laminar elements composed of a first PTC composition and, sandwiched between them, a laminar element composed of a second PTC composition having a higher resistivity than the first.

When a PTC device is tripped, most of the voltage dropped over the device is normally dropped over a relatively small part of the device which is referred to as the hot line, hot plane or hot zone. In the devices of the invention, the PTC element can have one or more features which help the hot line to form at a desired location, usually spaced apart from both electrodes. Suitable features of this kind for use in the present invention are disclosed for example in U.S. Pat. Nos. 4,317,027 and 4,352,083 (Middleman et al), U.S. Pat. Nos. 4,907,340 and 4,924,072 (Fang et al), the disclosures of which are incorporated herein by reference.

Laminar Electrodes

Particularly useful devices of the invention comprise two metal foil electrodes, and a PTC conductive polymer element sandwiched between them, especially such devices which are used as circuit protection devices and have low resistance at 23° C., generally less than 50 ohm, preferably less than 15 ohm, more preferably less than 10 ohm, particularly less than 5 ohm, especially less than 3 ohm, with yet lower resistance being possible, e.g. less than 1 ohm, even less than 0.5 ohm. Particularly suitable foil electrodes are microrough metal foil electrodes, including in particular electrodeposited nickel foils and nickel-plated electrodeposited copper foil electrodes, in particular as disclosed in U.S. Pat. No. 4,689,475 (Matthieson) and U.S. Pat. No. 4,800,253 (Kleiner et al), the disclosure of each of which is incorporated herein by reference. A variety of laminar deices which can be modified in accordance with the present invention are disclosed in U.S. Pat. No. 4,238,812 (Middleman et al), U.S. Pat. No. 4,255,798 (Simon), U.S. Pat. No. 4,272,471 (Walker), U.S. Pat. No. 4,315,237 (Middleman et al), U.S. Pat. No. 4,317,027 (Middleman et al), U.S. Pat. No. 4,330,703 (Horsma et al), U.S. Pat. No. 4,426,633 (Taylor), U.S. Pat. No. 4,475,138 (Middleman et al), U.S. Pat. No. 4,724,417 (Au et al), 4,780,598 (Fahey et al), 4,845,838 (Jacobs et al), 4,907,340 (Fang et al), and U.S. Pat. No. 4,924,074 (Fang et al), the disclosure of each of which is incorporated herein by reference. The electrodes can be modified so as to produce desired thermal effects.

The electrodes are preferably secured directly to the PTC resistive element.

Detailed Description of the Devices, Assemblies and Methods of the Invention in which a Cross-Conductor is Employed Apertures and Cross-Conductors The term "aperture" when used herein in connection with a device of the invention or an assembly of the invention to be converted into a plurality of devices of the invention (but not when used herein in connection with the apertures in a circuit board), denotes an opening which (a) has a closed cross section, e.g. a circle, an oval, or a generally rectangular shape, or (b) has an open reentrant cross section which (i) has a depth at least 0.15 times, preferably at least 0.5 times, particularly at least 1.2 times, the maximum width of the cross section, e.g. a quarter circle or a half circle or an open-ended slot, and/or (ii) has at least one part where the opposite edges of the cross section are parallel to each other.

In assemblies of the invention which can be converted into a plurality of electrical devices by dividing them along a plurality of lines of division, the apertures will normally be of closed cross section, but if one or more of the lines of division passes through an aperture of closed cross section, then the apertures in the resulting devices will then have open cross sections. It is important that any such open cross section is a reentrant cross section as defined above, in order to ensure that the cross-conductor is not damaged or dislodged during installation or use of the device.

The aperture can be a circular hole, and for many purposes this is satisfactory in both individual devices and assemblies of devices. However, if the assembly includes apertures which are traversed by at least one line of division, elongate apertures may be preferred because they require less accuracy in the lines of division.

When the aperture is not traversed by a line of division, it can be as small as is convenient for a cross-conductor having the necessary current-carrying capacity. For circuit protection devices, holes of diameter 0.1 to 5 mm, preferably 0.15 to 1.0 mm, e.g. 0.2 to 0.5 mm, are generally satisfactory. Generally a single cross-conductor is all that is needed to make an electrical connection to the first electrode from the opposite side of the device. However, two or more cross-conductors can be used to make the same connection. The number and size of the cross-conductors, and, therefore, their thermal capacity, can have an appreciable influence on the rate at which a circuit protection device will trip.

The aperture can be formed before the cross-conductor is put in place, or the formation of the aperture and the placing of the cross-conductor can be carried out simultaneously. A preferred procedure is to form the aperture, e.g. by drilling, slicing or any other appropriate technique, and then to plate or otherwise coat or fill the interior surface of the aperture. The plating can be effected by electroless plating, or electrolytic plating, or by a combination of both. The plating can be a single layer or multiple layers, and can be composed of a single metal or a mixture of metals, in particular a solder. The plating will often also be formed on other exposed conductive surfaces of the assembly. If such plating is not desired, then the other exposed conductive surfaces must be masked or otherwise desensitized. Generally, however, the plating is carried out at a stage of the process at which such additional plating will not produce an adverse effect. The invention includes the possibility that the plating will produce not only the cross-conductor but also at least part of the laminar conductive members in the device.

The plating techniques which are used for making conductive vias through insulating circuit boards can be used in the present invention. However, in this invention the plating serves merely to convey current across the device, whereas a plated via must make good electrical contact with another component. Consequently, the plating quality required in this invention may be less than that required for a via.

Another technique for providing the cross-conductors is to place a moldable or liquid conductive composition in preformed apertures, and if desired or necessary to treat the composition, while it is in the apertures, so as to produce cross-conductors of desired properties. The composition can be supplied selectively to the apertures, e.g. by means of a screen, or to the whole assembly, if desired after pretreating at least some of the assembly so that the composition does not stick to it. For example, a molten conductive composition, e.g. solder, could be used in this way, if desired using wave soldering techniques; and apertures in a PTC ceramic element could be filled with a conductive ceramic paste which was fired or otherwise consolidated in situ.

The cross-conductor can also be provided by a preformed member, e.g. a metal rod or tube, for example a rivet. When such a preformed member is used, it can create the aperture as it is put in place in the device.

The cross-conductor can partially or completely fill the aperture. When the aperture is partially filled, it can be further filled (including completely filled) during the process in which the device is connected to other electrical components, particularly by a soldering process. This can be encouraged by providing additional solder in and around the aperture, especially by including a plating of solder in and around the aperture. Normally at least a part of the cross-conductor will be put in place before the device is connected to other electrical components. However, the invention includes the possibility that the cross-conductor is formed during such a connection process, as for example by the capillary action of solder during a soldering process.

Assemblies

As briefly noted above, the assemblies of the invention containing cross-conductors include both devices which are ready for connection to other electrical components and structures which (if necessary after further processing) can be divided into a plurality of electrical devices.

In the devices which are ready for connection, the "first laminar conductive member" (to which the cross-conductor is physically and electrically connected) provides the first electrode, and the device generally also includes a second laminar conductive member which is not connected to the first electrode or the cross-conductor and which provides the second electrode. The first and second electrodes are generally secured, directly or indirectly, to opposite faces of a laminar PTC element, and the current-carrying part of the PTC element is that part which lies between the two electrodes. Preferably the device also includes a third laminar conductive member which (a) is secured to the second face of the PTC element in the area of the aperture, (b) is electrically connected to the cross-conductor, and (c) is spaced apart from the second electrode. Thus this third member provides a conductive pad through which connection can be made to the first electrode (via the cross-conductor) and which is easier to make a connection to than the cross-conductor alone. This third member is preferably a residual member formed by removing a part of a laminar conductive member, in particular from one laminar conductive member of an assembly comprising two laminar conductive members and a PTC element between them; the other part of the conductive member provides the second electrode. The shape of the third member, and of the gap between the third member and the second electrode, can be varied to suit the desired characteristics of the device and for ease of manufacture. Thus the third member is conveniently a small rectangle at one end of a rectangular device, separated from the second electrode by a rectangular gap, as shown for example in FIGS. 1 and 2; but other arrangements are possible. For example the third member can be an island separated from the second electrode by a gap of closed cross section. If two or more devices in parallel are needed there can be two or more second electrodes on the second face of the PTC element, with a single first electrode which is on the first face of the PTC element and to which connection is made via the cross-conductor. When two or more devices in series are required, the third member of one device can be connected to the second electrode of the adjacent device; the devices can be joined together by non-current-carrying sections of the PTC conductive polymer element, or otherwise.

Figure 2:
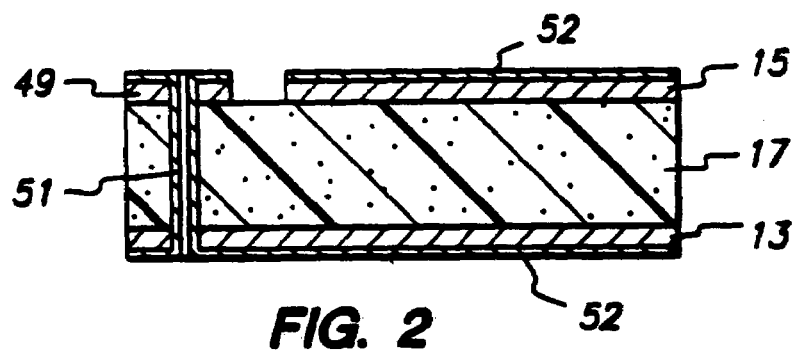
Figure 5:
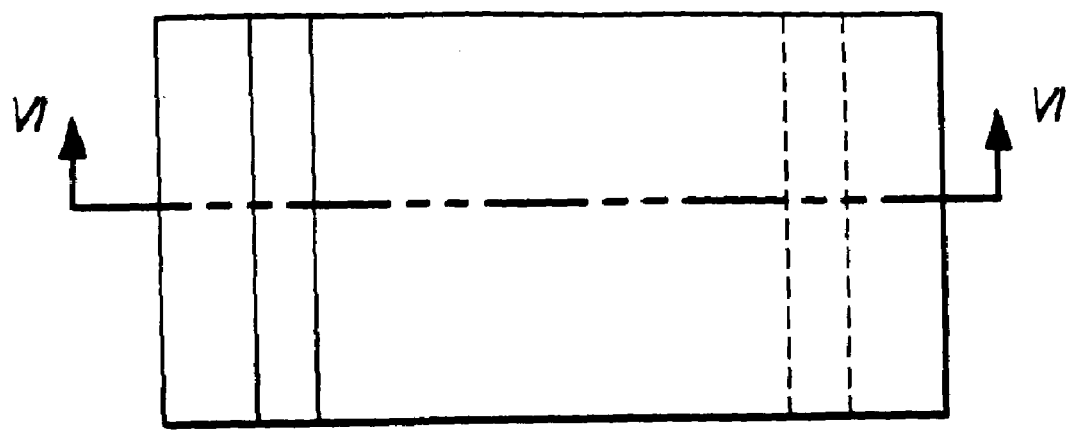
FIGS. 5 and 6 are plan and cross sectional views of a device of the invention containing a cross-conductor and mounted on a printed circuit board parallel to the board.
Figure 6:
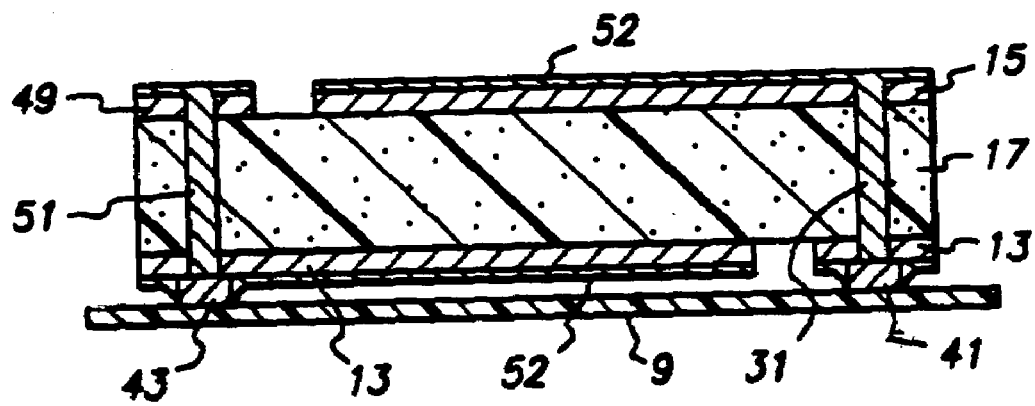

In the simplest devices, there is a single first electrode, a single cross-conductor, a single third member, and a single second electrode. Such a device is illustrated in FIGS. 1 and 2. A disadvantage of such a device is that it must be placed on the circuit board the right way up. This disadvantage can be overcome (at the expense of additional material and processing costs) by making a device which has two third members (one associated with each electrode) and two cross-conductors (one associated with each third member). Such a device is illustrated in FIGS. 5 and 6.

A particularly preferred embodiment of this invention is a circuit protection device which has a resistance of less than 15 ohm, preferably less than 10 ohm, particularly less than 5 ohm, especially less than 1 ohm, and which comprises (1) a laminar PTC resistive element which
   (a) is composed of a conductive polymer which has a resistivity at 25° C. of less than 50 ohm-cm, preferably less than 10 ohm-cm, particularly less than 5 ohm-cm, and which exhibits PTC behavior, and
   (b) has a first face and second face;
(2) a first metal foil electrode which contacts the first face of the PTC element;
(3) a second metal foil electrode which contacts the second face of the PTC element; and (4) an additional metal foil conductive member which contacts the second face of the PTC element and is spaced apart from the second electrode;

the PTC element, the first electrode and the additional conductive member defining an aperture which runs between the first electrode and the additional conductive member, through the PTC element; and (5) a transverse conductive member which
   (a) is composed of metal,
   (b) lies within the aperture, and
   (c) is physically and electrically connected to the first electrode and the additional conductive member.

The devices of the invention which contain cross-conductors and which are ready for connection can be of any appropriate size. However, it is an important advantage of this aspect the invention that very small devices can be easily prepared. Preferred devices have a maximum dimension of at most 12 mm, preferably at most 7 mm, and/or a surface area of at most 30 mm$^2$, preferably at most 20 mm$^2$, especially at most 15 mm$^2$.

In the assemblies of the invention which contain cross-conductors and which, if necessary after further processing, can be divided into a plurality of devices, preferably (a) the PTC resistive element defines a plurality of the apertures running between the first and second faces of the PTC element, (b) there are a plurality of the transverse conductive members, each of the transverse members lying within one of the apertures, and (c) the apertures and the transverse members are arranged in a regular pattern.

Generally the assembly further comprises (3) a first laminar conductive member which (a) is secured to the first face of the PTC element, and (b) is physically and electrically connected to all the transverse members; and (4) a second laminar conductive member which is secured to the second face of the PTC element.

The transverse members can also be physically and electrically connected to a second laminar conductive member. The first and/or second conductive members, before the assembly is divided and before or after the transverse members are put in place, are preferably in the form of a plurality of strips, arranged so that the assembly can be divided, along lines parallel to the strips, into devices which comprise first and second electrodes and a third member which is on the same face of the PTC element as the second electrode but is not connected to the second electrode.

Processes

The devices of the invention containing cross-conductors can be prepared in any way. However, the preferred methods of the invention make it possible to prepare devices very economically by carrying out all or most of the process steps on a large laminate, and then dividing the laminate into a plurality of individual devices, or into relatively small groups of devices which are connected together physically and which may be connected to each other electrically, in series or in parallel or both. The division of the laminate can be carried out along lines which pass through one or both or neither of the laminar conductive members or through none, some or all of the cross-conductors. The process steps prior to division can in general be carried out in any convenient sequence. Preferred processes for making the devices are disclosed in U.S. patent Ser. Nos. 08/242,916 and 08/257,586, both now abandoned, the subject matter of which is in U.S. Pat. Nos. 5,831,510 and 5.864,281, respectively, incorporated by reference herein.

Drawings Illustrated Devices Containing Cross-Conductors

The invention is illustrated in the accompanying drawings, in which the size of the apertures and the thicknesses of the components have been exaggerated in the interests of clarity. FIG. 1 is a plan view of a circuit protection device of the invention, and FIG. 2 is a cross section on line II—II of FIG. 1. The device includes a laminar PTC element 17 having a first face to which first laminar electrode 13 is attached and a second face to which second laminar electrode 15 is attached. Also attached to the second face is an additional laminar conductive member 49 which is not electrically connected to electrode 15. Cross-conductor 51 lies within an aperture defined by first electrode 13, PTC element 17 and additional member 49. The cross-conductor is a hollow tube formed by a plating process which also results in a plating 52 on the surfaces of the device which were exposed during the plating process.

Figure 3:
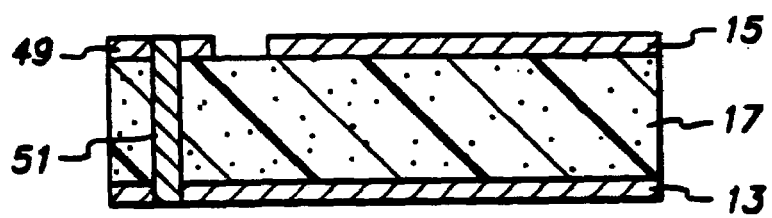
FIGS. 3 and 4 are cross sectional views of devices of the invention containing a cross-conductor.
Figure 4:
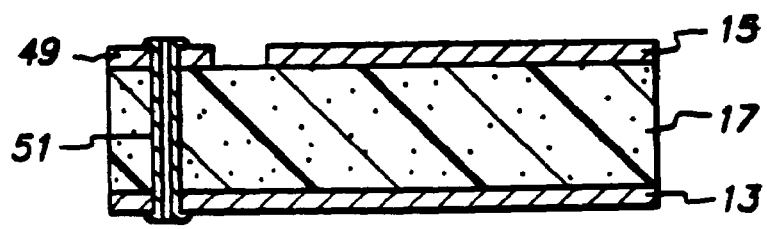

FIGS. 3 and 4 are similar to FIG. 2 but show cross-conductors which are in the form of a metal rod (FIG. 3) or a rivet (FIG. 4).

FIG. 5 is a plan view of another circuit protection device of the invention which has been soldered to a circuit board, and FIG. 6 is a cross section on line VI—VI of FIG. 5. The device is similar to that shown in FIGS. 1 and 2 but has been made symmetrical so that it can be placed on a circuit board either way up. Thus the device includes a second cross-conductor 31 which connects the second electrode 15 to a second additional member 35. The cross-conductors were made by plating the apertures (and the other exposed surfaces) first with copper and then with solder. The device has been soldered to traces 41 and 43 on an insulating substrate 9. During the soldering process the solder plating on the device flows and completely fills the apertures.

Figure 7:
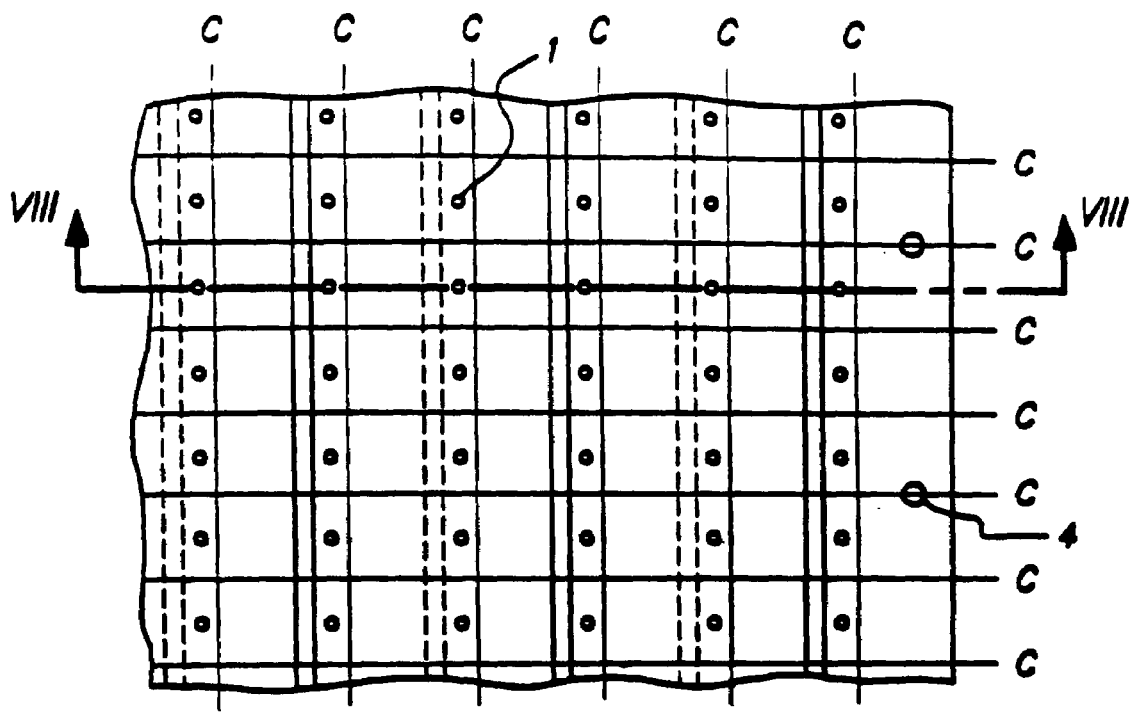
FIGS. 7 and 8 are plan and cross sectional views of part of an assembly of the invention which can be divided into a plurality of individual devices of the invention containing a cross-conductor.
Figure 8:
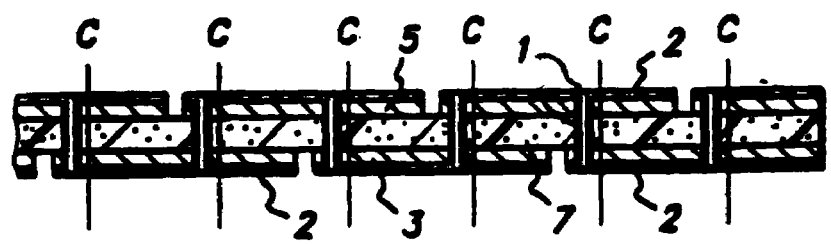

FIG. 7 is a plan view of a part of an assembly of the invention which can be divided into a number of individual devices as shown in FIGS. 1 and 2, and FIG. 8 is a cross section on line VIII—VIII of FIG. 7. The assembly includes a laminar PTC element 7 having a first face to which first laminar conductive member 3 is attached and a second face to which second laminar conductive member 5 is attached. The conductive members 3 and 5 are not continuous but are in the form of parallel strips formed by removing, e.g. by etching, strips of electrode material from a corresponding continuous member. The material is removed in staggered strips alternately from opposite sides of the assembly, in order to balance the physical stresses in the product. Before the etching step, a plurality of holes, arranged in a regular pattern, have been drilled through the PTC element 7 and the laminar members 3 and 5, and the assembly has then been plated to provide a tubular cross-conductor 1 in each of the apertures (and a plating 2 on other exposed surfaces of the assembly). The assembly can be converted into a plurality of devices by dividing it along the lines marked C. At the edge of the assembly, there are registration holes 4 for use in locating the holes to be drilled through the element 7 and members 3 and 5, and in locating the lines of division C.

Example Illustrating Devices Containing Cross-Conductors

EXAMPLE 1

A conductive polymer composition was prepared by pre blending 48.6% by weight high density polyethylene (Petrothene™ LB 832, available from USI) with 51.4% by weight carbon black (Raven™ 430, available from Columbian Chemicals), mixing the blend in a Banbury™ mixer, extruding the mixed compound into pellets, and extruding the pellets though a 3.8 cm (1.5 inch) extruder to produce a sheet with a thickness of 0.25 mm (0.010 inch). The extruded sheet was cut into 0.31×0.41 meter (12×16 inches) pieces and each piece was stacked between two sheets of 0.025 mm (0.001 inch) thick electrodeposited nickel foil (available from Fukuda). The layers were laminated under heat and pressure to form a plaque with a thickness of about 0.25 mm (0.010 inch). Each plaque was irradiated to 10 Mrad. Each plaque was used to prepare approximately 7000 devices, each having the configuration shown in FIGS. 1 and 2.

Holes with a diameter of 0.25 mm (0.010 inch) were drilled through the thickness of the plaque in a regular pattern to provide one hole for each device. Each hole was deburred and cleaned. The surface of both the nickel foil layers and the conductive polymer surrounding the drilled hole were sensitized using a palladium/copper solution. A copper layer approximately 0.076 mm (0.003 inch) thick was electroless plated onto the sensitized surfaces and then a 0.025 mm (0.001 inch) thick layer of tin-lead solder was electroless plated onto the copper surface. Using the following standard photoresist process, a pattern was etched onto the plaque. First, a dry film (Mylar™ polyester) resist was laminated onto both surfaces of the plaque and then exposed to ultraviolet light to generate a pattern as shown in FIGS. 7 and 8. Second, a ferric chloride solution was used to chemically etch the pattern. During this step, alternating sections on each side of the plaque were etched away to expose the solder and relieve built-up mechanical stress. Third, the etched plaque was rinsed and the resist was stripped away.

The plaque was sheared and diced to produce individual rectangular electrical devices. Each device had dimensions of 4.57×3.05×0.51 mm (0.180×0.120×0.020 inch). The through-hole was positioned approximately 3.81 mm (0.015 inch) from the shorter edge of the device. A strip of exposed conductive polymer 0.51×3.05 mm (0.020×0.120 inch) was present 0.38 mm (0.015 inch) from the through-hole and 1.02 mm (0.040 inch) from the shorter edge of the device. Each device had a resistance of approximately 300 mohm.

Detailed Description of the Devices, Assemblies and Methods of the Invention in which a Cross-Conductor is Not Necessarily Employed Devices In one aspect, referred to herein as Aspect A, the present invention provides an electrical device which comprises
 (1) a first laminar electrode;
 (2) a second laminar electrode; and
 (3) a laminar resistive element which exhibits PTC behavior, and which has a first face to which the first electrode is secured and an opposite second face to which the second electrode is secured;
 the device comprising
 (a) a main portion which comprises
  (i) a main part of the first electrode,
  (ii) a main part of the second electrode, and
  (iii) a main part of the resistive element; and
 (b) a first connection leg which extends away from the main portion and which comprises
  (i) a first leg part of the first electrode which is integral with the main part of the first electrode, and
  (ii) a first leg part of the resistive element which is integral with the main part of the resistive element.

The first connection leg can also include a first leg part of the second electrode which is integral with the main part of the second electrode. Preferably, however, the first connection leg includes a residual part of the second electrode which is not connected to the main part of the second electrode and which does not, therefore, play any part of the electrical operation of the device. Alternatively, the first leg can consist essentially of the first leg part of the first electrode and the first leg part of the resistive element.

First Embodiment of Aspect A of the Invention

In this embodiment, the device is designed to be mounted in apertures of a substrate, e.g. a printed circuit board.

The devices of this embodiment preferably also contain
 (c) a second connection leg which extends away from the main portion, which is spaced away from the first connection leg, and which comprises
  (i) a second leg part of the second electrode which is integral with the main part of the second electrode, and
  (ii) a second leg part of the resistive element which is integral with the main part of the resistive element.

The second leg can include a second leg part of the first electrode, but preferably includes only a residual part of the first electrode which provides useful physical properties but does not play any part in the electrical operation of the device. Alternatively the second leg can consist essentially of the second leg part of the second electrode and the second leg part of the resistive element. The main portion and the first and second connection legs are preferably substantially coplanar. However, one or both of the legs (or the sole leg, when there is only one) can be inclined to main portion. Generally each of the legs will extend away from the main portion by a distance of at least 0.15 cm, e.g. 0.15 to 1.0 cm, preferably 0.2 to 0.6 cm.

The first and second connection legs preferably extend away from the main portion in substantially the same direction so that they can both be mounted on a planar substrate, with the main portion of the device extending away from the substrate, preferably at right angles thereto.

In these devices, it is preferred that the first connection leg comprises a first distal sub-portion spaced away from the main portion of the device and a first stand-off sub-portion which lies between the first distal sub-portion and the main portion, and the second connection leg comprises a second distal sub-portion spaced away from the main portion of the device and a second stand-off sub-portion which lies between the second distal sub-portion and the main portion, with the distal and stand-off sub-portions being shaped so that when each of the distal sub-portions is placed in an aperture of an appropriate size in the planar substrate, the stand-off sub-portions will not pass through the apertures and will prevent contact between the substrate and the main portion of the device. Thus one or (preferably) both of the first and second connection legs can be wedge-shaped or can include a step which lies at the junction between the distal and stand-off sub-portions.

When the device is prepared merely by cutting it out from a uniform laminate of the electrode materials and the resistive material, the device will be one in which (a) the first leg part of the first electrode, the first leg part of the resistive element, and a first leg part of the second electrode are substantially coextensive, and (b) a second leg part of the first electrode, the second leg part of the resistive element, and the second leg part of the second electrode are substantially coextensive.

In some cases, however, it is preferred that the device should be one in which the first stand-off sub-portion comprises a first bridge sub-portion which extends across the width of the first connection leg and which does not include any part of the second electrode; and the second stand-off sub-portion comprises a second bridge sub-portion which extends across the width of the second connection leg and does not include any part of the first electrode. Such a device can be prepared by removing a portion of the second electrode from the first connection leg and by removing a portion of the first electrode from the second connection leg, to give a device in which the first distal sub-portion comprises a second residual conductive member which, in the absence of the first bridge sub-portion, would be integral with the main part of the second electrode; and the second distal sub-portion comprises a first residual conductive member which, in the absence of the second bridge sub-portion, would be integral with the main part of the first electrode. In a device prepared in this way, the second residual conductive member is preferably separated from the second electrode by a distance which is at least as great as the minimum distance between the first and second electrodes at any location on the device, e.g. 1.5 to 4 times that distance, and the first residual conductive member is preferably separated from the first electrode by a distance which is at least as great as the minimum distance between the first and second electrodes at any location on the device, e.g. 1.5 to 4 times that distance. The portion of the electrode which is removed can have a simple shape, e.g. a rectangular strip, or a more complex shape. We have found that the physical strength of the leg can be improved by removing a more complex shape, e.g. a V-shaped portion, of the electrode.

Such a device can also be prepared by removing all of the second electrode from the first connection leg and all of the first electrode from the second connection leg, or by using corresponding preshaped electrodes, in which case the first connection leg is free from any conductive member which, in the absence of the first bridge sub-portion, would be integral with the main part of the second electrode; and the second connection leg is free from any conductive member which, in the absence of the second bridge sub-portion, would be integral with the main part of the first electrode.

Second Embodiment of Aspect A of the Invention

In this embodiment, the device is designed to be mounted parallel to, preferably spaced apart by a small distance from, a substrate, e.g. a printed circuit board.

In the devices of this embodiment, the first connection leg comprises (i) a first distal sub-portion which
  (a) is spaced away from the main portion of the device,
  (b) comprises a first distal sub-part of the first leg part of the first electrode, and
  (c) comprises a first electrical connector which contacts the first distal sub-part of the first electrode and extends at least to the second face of the laminar resistive element; and (ii) a first bridge sub-portion which
  (a) lies between the first distal sub-portion and the main portion of the device,
  (b) extends across the width of the first connection leg, and
  (c) does not include any part of the second electrode;

whereby the device can be placed flat on a planar insulating substrate having first and second appropriately spaced-apart metal conductors on the surface thereof, with the first electrical connector adjacent the first metal conductor; and electrical connection can be made (a) between the first metal conductor and the first electrode, through the first electrical connector, and (b) between the second conductor and the second electrode.

Such a device can be made by removing a strip of the second electrode from the first connection leg, to give a device in which the first distal sub-portion comprises a second residual conductive member which is on the second face of the first leg part of the resistive element and which, in the absence of the first bridge sub-portion, would be integral with the main part of the second electrode.

The first electrical connector is preferably a cross-conductor as described in detail above. However, it can be of any kind, for example a connector which will remain in place even if it is not bonded to the other parts of the device, for example a U-shaped member which extends around the end of the first leg portion and the first electrode and, if present, the second residual conductive member. The connector can be resilient so that it clamps to the remainder of the device.

So that the device can be placed either way up on the substrate, and/or so that it has balanced electrical properties, the device preferably also contains a second connection leg which extends away from the main portion of the device; which is spaced apart from the first connection leg; which comprises (i) a second leg part of the second electrode which is integral with the main part of the second electrode, and (ii) a second leg part of the resistive element which is integral with the main part of the resistive element;

and which comprises (iii) a second distal sub-portion which
  (a) is spaced apart from the main portion of the device,
  (b) comprises a second distal sub-part of the second leg part of the second electrode, and
  (c) comprises a second electrical connector which contacts the second distal sub-part of the second electrode and extends at least to the first face of the laminar resistive element; and (iv) a second bridge sub-portion which
  (a) lies between the second distal sub-portion and the main portion of the device,
  (b) extends across the width of the second connection leg, and
  (c) does not include any part of the first electrode;

whereby the device can be placed flat on a planar insulating substrate having first and second appropriately spaced apart metal conductors on the surface thereof, with either the first electrical connector or the second electrical connector adjacent one of the metal conductors, and electrical connection can be made between (a) said electrical connector and metal conductor and (b) the other metal conductor and the electrode adjacent to the substrate.

The preferred characteristics of the second distal and bridge sub-portions and the second connection part are substantially the same as previously described for the first distal and bridge sub-portions and the first connector.

In these devices the contacting surfaces are preferably coated with solder or tin, or otherwise treated, so that they can all be soldered together in a single step by exposing them to heat.

Assemblies

Aspect B

In another aspect, referred to herein as Aspect B, the invention provides an electrical assembly which comprises
- (A) an insulating substrate having a first aperture therein;
- (B) a first metal conductor secured to the insulating substrate and leading to the first aperture; and
- (C) an electrical device which comprises
  - (1) a first laminar electrode;
  - (2) a second laminar electrode; and
  - (3) a laminar resistive element which exhibits PTC behavior and which has a first face to which the first electrode is secured and an opposite second face to which the second electrode is secured;

the device comprising
- (a) a main portion which comprises
  - (i) a main part of the first electrode,
  - (ii) a main part of the second electrode, and
  - (iii) a main part of the resistive element; and
- (b) a first connection leg
  which extends away from the main portion,
  which comprises
  - (i) a first leg part of the first electrode which is integral with the main part of the first electrode, and
  - (ii) a first leg part of the resistive element which is integral with the main part of the resistive element, and
  which has a first distal sub-portion spaced away from the main portion of the device and a first stand-off sub-portion between the first distal sub-portion and the main portion;

the first distal sub-portion including a first distal sub-part of the first electrode and lying within the first aperture of the substrate;

the first stand-off sub-portion lying between the substrate and the main portion of the device;

the first metal conductor being physically and electrically connected to the first distal sub-part of the first electrode; and all of the electrical current between the first metal conductor and the second electrode of the device passing though the first electrode and the resistive element.

Preferably the insulating substrate has a second aperture therein; a second metal conductor is secured to the insulating substrate and leads to the second aperture; and the device also contains a second connection leg which
- (a) extends away from the main portion,
- (b) is spaced away from the first connection leg,
- (c) comprises
  - (i) a second leg part of the second electrode which is integral with the main part of the second electrode, and
  - (ii) a second leg part of the resistive element which is integral with the main part of the resistive element, and
- (d) has a second distal sub-portion spaced away from the main portion of the device and a second stand-off sub-portion between the second distal sub-portion and the main portion;

the second distal sub-portion including a second distal sub-part of the second electrode and lying within the second aperture of the substrate;

the second metal conductor being physically and electrically connected to the second distal sub-part of the second electrode; and all of the electrical current between the second metal conductor and the first electrode of the device passing through the second electrode and the resistive element.

In one preferred assembly, the first leg part of the first electrode, the first leg part of the resistive element, and the first leg part of the second electrode are substantially coextensive; the second leg part of the first electrode, the second leg part of the resistive element, and the second leg part of the second electrode are substantially coextensive; the first conductor terminates on one side of the first aperture and is connected by a first solder joint to the first leg part of the first electrode, with the distance between any part of the first solder joint and the second electrode being at least as great as the minimum distance between the first and second electrodes at any location on the device, e.g. 1.5 to 4 times that distance; and the second conductor terminates on one side of the second aperture and is connected by a second solder joint to the second leg part of the second electrode, with the distance between any part of the second solder joint and the first electrode being at least as great as the minimum distance between the first and second electrodes at any location on the device, e.g. 1.5 to 4 times that distance.

In another preferred assembly
- (a) the first stand-off sub-portion comprises a first bridge sub-portion which extends across the width of the first connection leg and which does not include any part of the second electrode
- (b) the second stand-off sub-portion comprises a second bridge sub-portion which extends across the width of the second connection leg and does not include any part of the first electrode;
- (c) the first distal sub-portion comprises a second residual conductive member which, in the absence of the first bridge sub-portion, would be integral with the main part of the second electrode;
- (d) the second distal sub-portion comprises a first residual conductive member which, in the absence of the second bridge sub-portion, would be integral with the main part of the first electrode; and
- (e) the first conductor is connected by a first solder joint to the first leg part of the first electrode, with the distance between any part of the first solder joint and the second electrode being at least as great as the minimum distance between the first and second electrodes at any location on the device; and the second conductor is connected by a second solder joint to the second leg part of the second electrode, with the distance between any part of the second solder joint and the first electrode being at least as great as the minimum distance between the first and second electrodes at any location on the device.

Aspect C

In another aspect, referred to herein as Aspect C, the invention provides an electrical assembly which comprises
- (A) a planar insulating substrate;
- (B) a first metal conductor secured to the insulating substrate;
- (C) a second metal conductor secured to the insulating substrate; and
- (D) an electrical device which comprises
  - (1) a first laminar electrode;
  - (2) a second laminar electrode; and
  - (3) a laminar resistive element which exhibits PTC behavior and which has a first face to which the first electrode is secured and an opposite second face to which the second electrode is secured;

the device comprising
(a) a main portion which comprises
  (i) a main part of the first electrode,
  (ii) a main part of the second electrode, and
  (iii) a main part of the resistive element; and
(b) a first connection leg
  which extends away from the main portion,
  which comprises
  (i) a first leg part of the first electrode which is integral with the main part of the first electrode,
  (ii) a first leg part of the resistive element which is integral with the main part of the resistive element,
  (iii) a first distal sub-portion which
    is spaced away from the main portion of the device,
    comprises a first distal sub-part of the first leg part of the first electrode, and
    comprises a first electrical connector which contacts the first distal sub-part of the first electrode and extends beyond the second face of the laminar resistive element; and
  (iv) a first bridge sub-portion which
    lies between the first distal sub-portion and the main portion of the device,
    extends across the width of the first connection leg, and
    does not include any part of the second electrode;

the device being placed generally parallel to the planar insulating substrate with the second electrode being closer to the substrate than the first electrode, the first electrical connector being connected to the first metal conductor; and the second electrical conductor being connected to the second electrode.

In such an assembly, the device preferably also contains a second connection leg which extends away from the main portion of the device; which is spaced apart from the first connection leg, which comprises
(i) a second leg part of the second electrode which is integral with the main part of the second electrode, and
(ii) a second leg part of the resistive element which is integral with the main part of the resistive element; and which comprises
(i) a second distal sub-portion which
  (a) is spaced apart from the main portion of the device,
  (b) comprises a second distal sub-part of the second leg part of the second electrode, and
  (c) comprises a second electrical connector which contacts the second distal sub-part of the second electrode and extends beyond the first face of the laminar resistive element; and
(ii) a second bridge sub-portion which
  (a) lies between the second distal sub-portion and the main portion of the device,
  (b) extends across the width of the second connection leg, and
  (c) does not include any part of the first electrode.

Preferably there is a solder joint between each of
(a) the first electrical connector and the first electrode,
(b) the first electrical connector and the first metal conductor, and
(c) the second electrode and the second metal conductor, or between the second electrode and an intermediate connector and between the intermediate connector and the second metal conductor, the intermediate connector lying between the second electrode and the second metal conductor.

Drawings Illustrating Devices which do not Contain Cross-Conductors

FIG. 9 shows an electrical assembly 1 of the invention and FIG. 10 shows a cross-section of electrical assembly 1 along line 2—2 of FIG. 9. In both FIGS. 9 and 10, an electrical device 3 of the invention is mounted into first aperture 5 and second aperture 7 on an insulating planar substrate 9, e.g. a circuit board. The section of electrical device 3 above line A—A is the main portion 11, in which the main part of the first laminar electrode 13 and the main part of the second laminar electrode 15, shown in these Figures as metal foil electrodes, are attached to the main part of the laminar resistive element 17, here a conductive polymer which exhibits PTC behavior. Device 3 comprises two connection legs 19 and 27 which are coplanar and extend away from main portion 11 and are used to insert device 3 into the substrate 9. First connection leg 19 comprises a first leg part of the first electrode and a first leg part of the resistive element. In addition, first connection leg 19 comprises a first distal sub-portion 21, a first stand-off sub-portion, shown here in the form of a step, and a first bridge sub-portion 25 (on the back surface of FIG. 1). Second connection leg 27 comprises a second stand-off sub-portion 29, second distal sub-portion 31 which lies at least partly within the second aperture 7, and second bridge sub-portion 33. Second distal sub-portion 31 includes the second distal subpart of the second electrode and lies within the second aperture 7 of the substrate. As shown in FIG. 10, below line A—A lie a first residual conductive member 35 which is part of the second connection leg 27, as well as the second leg part of the second electrode 37 and the second leg part of the resistive element 39. In order to make electrical contact to the electrical device 3, connection is made between the electrical device 3 and the first metal conductor 41, a conductive trace which leads to the first aperture and is secured to the substrate, and between the electrical device 3 and the second metal conductor 43 which leads to the second aperture and is secured to the substrate. As shown in FIG. 10, solder 45 is used to make connection between second metal conductor 43 and the second laminar electrode 15, as well as between the second metal conductor 43 and the residual part of the electrode 13.

FIG. 11 shows a plan view of another electrical assembly 1 of the invention, FIG. 12 shows a cross-section of electrical assembly 1 along line 4—4 of FIG. 11, and FIG. 13 is a bottom view of the assembly of FIG. 11 along line 5—5 before and after insertion and electrical connection of a device of the invention. As shown in FIGS. 9 and 10, electrical device 3 is inserted onto insulating planar substrate 9 through first aperture 5 and second aperture 7 by means of first connection leg 19 and second connection leg 27, respectively. For this device, the first connection leg 19 and the second connection leg 27 are in the form of wedges, and neither a first bridge sub-portion nor a second bridge-sub-portion is present. In FIG. 12, the second distal sub-portion 31 of the second connection leg 27 is visible, and, below line A—A, the second leg part of the first electrode 37 and the second leg part of the resistive element 39 are shown. First metal conductor 41 leads to and terminates on one side of first aperture 5, and second metal conductor 43 leads to and terminates on the opposite side of second aperture 7. As shown in FIG. 12, electrical connection is made between the first laminar electrode 13 and the first metal conductor 43 by means of solder joint 47.

FIG. 14 is a top view of another assembly 1 of the invention and FIG. 15 is a cross-sectional view through the thickness of the assembly 1 in which the electrical device 3 is suitable for installing as a surface mounted device. In this assembly, the electrical device 3 comprises a laminar resistive element 61 which is laminated to the main portion of the first electrode 13 and the first residual conductive member 35 and to the main portion of the second electrode 15 and the second residual conductive member 49. (The main portion 11 of the device lies between lines C and D.) Attached to first connection leg 19 around first distal sub-portion 21 is U-shaped first connector 51. Attached to second connection leg 27 around second distal sub-portion 31 is U-shaped second connector 53. A solder joint 59 lies between the periphery of the first connector 51 and the first electrode 13 and between the periphery of the second connector 53 and the second electrode 15. First bridge sub-portion 25 lies between lines D and E and second bridge sub-portion 33 lies between lines B and C. Electrical connection is made from the first connector 51 to a first metal conductor 41 secured to insulating substrate 9 by means of first solder joint 55, and from the second connector 53 to second metal connector 43 secured to the insulating substrate 9 by means of second solder joint 57.

Examples Illustrating Devices which do not Contain Cross-Conductors

EXAMPLE 2

A conductive polymer composition was prepared by pre blending 48.6% by weight high density polyethylene (Petrothene LB832, available from USI) with 51.4% by weight carbon black (Raven 430, available from Columbian Chemicals). The blend was mixed in a Banbury mixer, and the resulting composition was extruded through a 63.5 mm (2.5 inch) extruder to form a sheet with a thickness of 0.51 mm (0.020 inch). Two sheets of extrudate were laminated together to give a sheet with a thickness of about 1 mm (0.040 inch). The sheet was laminated on each side with 0.025 mm (0.001 inch) thick electrodeposited nickel foil (available from Fukuda) and the laminate was irradiated to a dose of 10 Mrad using a 4.5 MeV electron beam. An electrical device with a shape as shown in FIG. 9 was cut from the irradiated sheet. The main portion had a width of approximately 7.75 mm (0.305 inch) and a length of approximately 19.7 mm (0.775 inch). The first connection leg and the second connection leg each had a length of 5.25 mm (0.207 inch). There was a maximum distance between the first and second connection legs at the first and second distal sub-portions of 3.8 mm (0.150) inch, and a distance between the step of the first standoff sub-portion and the step of the second standoff sub-portion of 2.0 mm (0.0 W inch). The length of the first bridge sub-portion on the first connection leg and of the second bridge sub-portion on the second connection leg was 1.27 mm (0.05 inch). The first and second bridge sub-portions were created by scoring the nickel foil and peeling it completely away from the conductive polymer resistive element.

The first and second connection legs of the electrical device were inserted into first and second apertures, respectively, of a printed circuit board to form an assembly. The assembly was then wave-soldered, causing the electrical traces on the circuit board leading to the first and second apertures to be connected by solder to the first and second connection legs, respectively, as shown in FIG. 10. Solder completely surrounded the first and second connection legs.

EXAMPLE 3

A conductive polymer composition was mixed, extruded, laminated, and irradiated as in Example 2. An electrical device with a shape as shown in FIG. 11 was cut from the irradiated sheet. The main portion had a width of approximately 7.8 mm (0.307 inch) and a length of 21 mm (0.827 inch). The first and second leg portions each had a length of 4 mm (0.157 inch) and tapered from a maximum of 2.5 mm (0.098 inch) at the junction with the main portion to a minimum of 1.75 mm (0.068 inch) at the first distal sub-portion and the second distal sub-portion. No bridge sub-portions were created.

The first and second connection legs of the electrical device were inserted into first and second apertures, as in Example 2. In this case, however, the electrical traces on the circuit board made contact with only one of the electrodes. Thus when the assembly was subjected to wave soldering, only one side of the device was electrically connected to each of the traces, as shown in FIGS. 12 and 13.

We claim:
1. An assembly which comprises
   (1) a PTC resistive element which
      (a) is composed of a resistive material which exhibits PTC behavior and has a resistivity at 25° C. of less than 10 ohm-cm,
      (b) has a first face and a second face, and
      (c) defines an aperture which runs between the first and second faces;
   (2) a transverse conductive member which
      (a) lies within the aperture defined by the PTC element,
      (b) runs between the first and second faces of the PTC element,
      (c) is secured to the PTC element; and
      (d) comprises metal; and
   (3) a first laminar conductive member which (a) is secured to the first face of the PTC element and (b) is physically and electrically connected to the transverse conductive member.
2. A circuit protection device which has a resistance of less than 15 ohm and a maximum dimension of at most 12 mm, and which comprises
   (1) a laminar PTC resistive element which
      (a) is composed of a conductive polymer which has a resistivity at 25° C. of less than 50 ohm-cm and which exhibits PTC behavior, and
      (b) has a first face and second face;
   (2) a first metal foil electrode which contacts the first face of the PTC element;
   (3) a second metal foil electrode which contacts the second face of the PTC element; and
   (4) an additional metal foil conductive member which contacts the second face of the PTC element and is spaced apart from the second electrode;
   the PTC element, the first electrode and the additional conductive member defining an aperture which runs between the first electrode and the additional conductive member, through the PTC element; and

(5) a transverse conductive member which
  (a) is composed of metal,
  (b) lies within the aperture, and
  (c) is physically and electrically connected to the first electrode and the additional conductive member.

3. An electrical assembly which comprises
(A) a printed circuit board including first and second conductive traces on a surface thereof, and
(B) an electrical device which comprises
  (1) a laminar PTC resistive element which
    (a) is composed of a resistive material which exhibits PTC behavior, and
    (b) has a first face and a second face;
  (2) a first laminar electrode which is secured to the first face of the PTC element;
  (3) a second laminar electrode which is secured to the second face of the PTC element;
  (4) an additional laminar conductive member which (a) is secured to the second face of the PTC element and (b) is spaced apart from the second electrode;
  the PTC element, the first electrode and the additional laminar conductive member defining an aperture which runs between the first electrode and the additional conductive member, through the PTC element; and
  (5) a transverse conductive member which
    (a) lies within the aperture, and
    (b) is physically and electrically connected to the first electrode and the additional conductive member;
  said electrical device being placed on the printed circuit board and parallel thereto, with the first conductive trace physically and electrically connected to the additional conductive member, and the second conductive trace physically and electrically connected to the second electrode.

4. An assembly which comprises
  (1) a laminar PTC resistive element which (i) is composed of a resistive material exhibiting PTC behavior and having a resistivity at 25° C. of less than 10 ohm-cm, and (ii) has a first face and a second face,
  (2) a first laminar conductive member which is secured to the first face of the PTC element, and
  (3) a second laminar conductive member which is secured to the second face of the PTC element;
  the PTC element and the first and second laminar conductive members defining a plurality of apertures which pass through the thickness of the assembly, and the apertures being arranged in a regular pattern.

* * * * *